United States Patent [19]
Gombocz et al.

[11] Patent Number: 5,217,591
[45] Date of Patent: Jun. 8, 1993

[54] GEL ELECTROPHORESIS SAMPLE APPLICATOR/RETRIEVER

[75] Inventors: Erich Gombocz, Menlo Park; Mark Dwight, Palo Alto; David H. Rammler, Woodside, all of Calif.

[73] Assignee: Labintelligence, Inc., Menlo Park, Calif.

[21] Appl. No.: 954,911

[22] Filed: Sep. 30, 1992

Related U.S. Application Data

[63] Continuation-in-part of Ser. No. 837,067, Feb. 14, 1992, and a continuation-in-part of Ser. No. 772,947, Oct. 8, 1991, and a continuation-in-part of Ser. No. 522,325, May 14, 1990, Pat. No. 5,104,512.

[51] Int. Cl.⁵ .................... G01N 27/26; G01N 27/447
[52] U.S. Cl. .......................... 204/299 R; 204/182.8; 204/180.1
[58] Field of Search .............. 204/299 R, 182.8, 182.7, 204/182.9, 180.1

[56] References Cited

U.S. PATENT DOCUMENTS 4,431,506  2/1984  Gorman, Jr. et al. .......... 204/299 R
5,139,637  8/1992  MacConnell .................... 204/182.8

OTHER PUBLICATIONS

J. Gershoni (1987) in *Advances in Electrophoresis*, vol. 1, pp. 143-175.
A. Andrews (1986) in *Electrophoresis: Theory Techniques and Biochemical and Clinical Applications*. 2nd Edition, pp. 24-25, 59-74, 188-192.

Primary Examiner—John Niebling
Assistant Examiner—John S. Starsiak, Jr.
Attorney, Agent, or Firm—Bertram I. Rowland

[57] ABSTRACT

A sample applicator/retriever for gel electrophoresis is provided, which allows easy and reproducible application or retrieval of samples. The sample nozzle is designed to load samples uniformly through a gel. The applicator/retriever may be in several different forms, including a a multiwell device, individual wells and mounting bar, a single line well, or a concentrator applicator.

11 Claims, 4 Drawing Sheets

GEL ELECTROPHORESIS SAMPLE APPLICATOR/RETRIEVER

CROSS-REFERENCE TO RELATED APPLICATIONS

This application is a continuation-in-part of application Ser. No. 07/837,067, filed Feb. 14, 1992, and application Ser. No. 07/522,325, filed May 14, 1990 now U.S. Pat. No. 5,104,512, and application Ser. No. 07/772,947, filed Oct. 8, 1991.

INTRODUCTION

1. Technical Field

The field of this invention is gel electrophoresis.

2. Background

With the huge expansion in biotechnology, gel electrophoresis has become an indispensable tool. The ability to separate nucleic acid fragments and proteins by means of size, shape and charge has added numerous opportunities to identify specific compounds, indicate purity, and allow for isolation of a compound in relatively pure form. By being able to change the conditions under which one carries out the electrophoresis, one can determine many characteristics of the compounds in the sample.

A variety of new techniques are predicated on the use of gel electrophoresis in an efficient and convenient way. Restriction fragment length polymorphisms is one application where one can perform genetic diagnosis by means of a genomic DNA sample. This technique may also be used in forensic medicine to identify the source of nucleic acids. Gel electrophoresis may also be used to identify a compound, by separation of a complex mixture and then by using markers such as antibodies, or the like. Electrophoresis is used in conjunction with transfer to a membrane such as Southern, Northern, and Western blotting, or other techniques involving transfer of the separated sample to a different substrate.

While much of the power of gel electrophoresis as a tool in identification and separation is realized, there are still many shortcomings. Apparatuses tend to be relatively large and cumbersome. Comparisons from samples or runs and particularly from different laboratories are very difficult since conditions of the electrophoresis vary and regulation and monitoring of the conditions is not available or unreliable. Thus, one frequently gets wide variation in determinations of molecular weight, as well as the properties of the sample components. Therefore, it has been very difficult to make comparisons from one run to another, no less from one laboratory to another.

Additionally, the gel electrophoretic apparatus usually does not prevent the sample from running off the gel, nor does it provide assurance that the sample has had sufficient time for a reasonable separation. Thus, substantial improvements in presently available equipment is desirable in order to obtain a satisfactory electrophoretic separation.

There is substantial interest in being able to provide electrophoretic systems which can be substantially automated, assure directly comparative results, and provide economies in the use of electrophoresis.

RELEVANT LITERATURE

References include J. Gershoni (1987) in *Advances in Electrophoresis*, Vol. 1, p. 143-175 and A. Andrews (1986) in *Electrophoresis: Theory, Techniques and Biochemical and Clinical Applications*, 2nd Edition, p. 24-25, 59-74, 188-192.

SUMMARY OF THE INVENTION

A sample applicator/retriever is provided, which allows easy and reproducible application or retrieval of a sample for gel electrophoresis. The same device may be used for both application and retrieval of samples. The sample nozzle is designed such that the sample is loaded uniformly throughout the thickness of the gel. The applicator/retriever may be formed with a plurality of wells. The wells may be sized for small sample volumes, or with a concentrator for large volumes. The device may also be in the form of an individual well applicator/retriever, whereby individual portions of samples subjected to gel electrophoresis may be applied or recovered. Another improvement is disclosed for a line applicator/retriever which allows the application of a single sample on a gel in the form of a uniform line.

DESCRIPTION OF THE SPECIFIC EMBODIMENTS

Figure 1A:
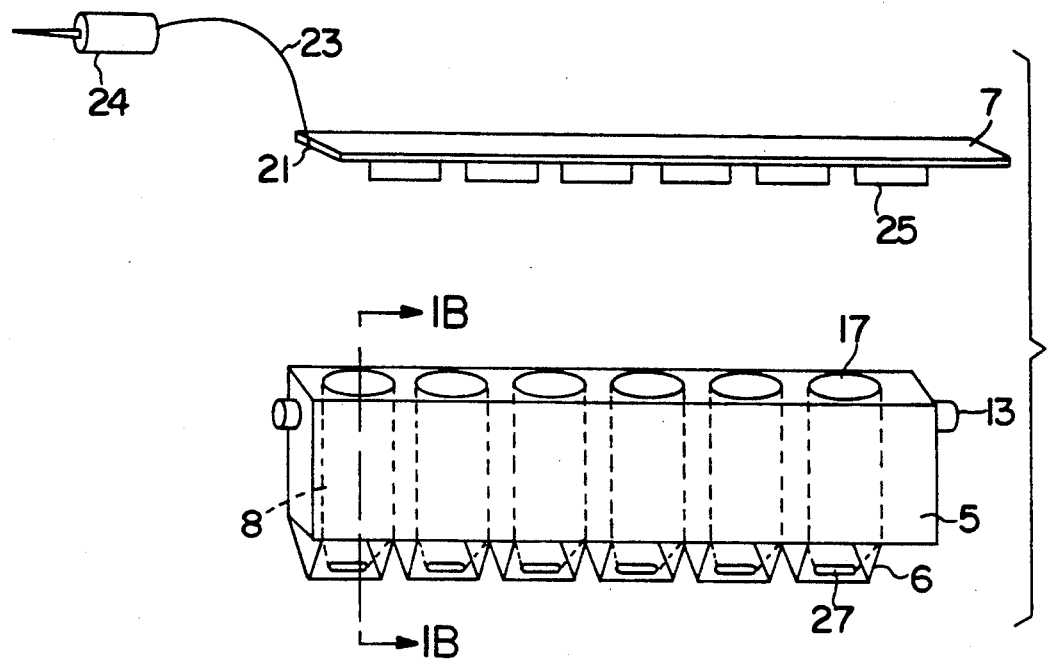
FIG. 1A is a perspective view of the multi-well applicator/retriever.

An gel electrophoresis applicator/retriever is provided which utilizes current flow to load samples evenly through a gel. The applicator/retriever may be formed with a plurality of wells, either fixed or removable, for loading multiple samples on a single gel. Other embodiments may have a single well for preparative or multi-dimensional gels. The use of a retrieval electrode with the applicator device allows samples to be electrophoresed out of the gel without complicated recovery procedures. The electrode may be removable, or embedded in the applicator.

The sample applicator/retriever device has the benefits of an applicator and a retriever used in combination with an electrophoresis system as described in U.S. patent application No. 07/837,067, filed Feb. 14, 1992 and provides the following advantages. The applicator and retriever is combined in one unit for more efficient and convenient use and manufacture. The applicator is converted into a retriever by the use of an optionally removable electrode. This electrode may also be used for active transport of sample components into the gel, if the electric field is inverted. The means for transferring the sample to the gel is improved. The applicator device now has a nozzle which contacts the gel, and through which the sample is transferred and evenly dispersed throughout the thickness of the gel.

The applicator device consists of a number of wells in a linear array. The number of wells will usually be equal to the number of lanes on the gel. Each well forms a channel which extends through the device, and is open at the top and bottom. The bottom of each channel forms a nozzle. The tip of the nozzle is inserted into the gel. The sample is introduced through the top of the well, and enters the gel through the opening in the nozzle.

The nozzle has a unique design which transfers the sample evenly through the thickness of the gel. The nozzle is triangular when viewed in a cross-section orthogonal to the array of wells, and comes to a point. The bottom edge is transverse to the surface of the gel, in the direction of migration of the sample when the sample is being applied. The front face of the triangle, which is angled to the gel surface, faces the direction in which a sample will migrate, and the back face, which is also angled to the gel surface, is away from the direction of migration. The nozzle opening, or aperture is on the front face.

In applying the sample, the nozzle is inserted through the surface of the gel to a depth not greater than 75% and not less than 25%, and usually about 50% of the thickness of the gel. When a current is applied to the gel, the presence of the nozzle causes a distortion in the electrical field lines for a short distance. The field lines become concentrated at the nozzle tip, and more dispersed closer to the gel surface. The distortion of the field lines may cause differential mobility of the sample at different depths in the gel. The angle of the front face of the nozzle, and the width of the aperture are optimized in such a way that the sample is evenly dispersed throughout the thickness of the gel.

After the sample is loaded, the applicator is removed from the gel, leaving some deformation in the structure of the gel due to the presence of the applicator. The back face of the nozzle is angled in such a way that the volume of space occupied by the nozzle in the gel is minimized, in order to decrease the amount of deformation, and allows for healing of the gel after removal of the nozzle.

The samples may be pre-loaded into the applicator wells in any suitable media. The sample will stay contained within the well by surface tension at the nozzle aperture. A stacking gel may be pre-cast in the well, if it is desirable that the sample be concentrated prior to loading. Samples with large volumes may be concentrated, or have an additional separation step by the use of a concentrator applicator, see U.S. Pat. No. 5,104,512. Any form of gel or separation matrix may be pre-cast in the concentrator well.

The applicator uses a chemically inert electrode to retrieve samples. The electrode may be an integral part of the applicator or, in a preferred embodiment, the electrode is provided on a removable retriever electrode bar which fits onto the applicator/retriever apparatus. The electrode is formed of an electrically conductive material, preferably platinum wire or graphite. The electrode material extends into the top of each of the wells.

For retrieval, there must be electrical communication between the electrode and the surface of the gel. The electrode may extend deep into the well, or the well may be filled with electroconductive media which contacts the electrode. The electroconductive media will usually be an aqueous salt solution, such as that used for a buffer during gel electrophoresis. A current is passed between the retriever electrode and one other electrode on the gel apparatus. The desired sample band is then electrophoresed from the gel into the well.

The lower end of the well may be filled with an absorbent retrieval matrix. This matrix performs several functions. The sample is usually retrieved into the matrix, and is thereby contained in a small volume. To prevent the sample from moving into the electroconductive buffer a stop buffer may used between the matrix and the electroconductive media. The matrix also acts to hold the electroconductive media in the well. The matrix may be formed of a wide variety of materials such as fiber, paper, sponge, gel or any number of such bibulous materials that will absorb a conductive, e.g. aqueous, media in the channels.

The applicator/retriever may have several embodiments for different uses. The multi-well applicator contains a plurality of wells in a fixed array. The number of wells will usually be equal to the number of lanes in the gel. The wells are designed to efficiently load sample volumes in the range of about 10 to 250 $\mu$l, usually about 10 to 50 $\mu$l. The well is usually cylindrical in shape, but may also be conical or any other convenient shape.

The individual well applicator/retriever also has a plurality of wells. However, the individual wells are not in a fixed array, but may be reversibly attached to a mounting bar. In this way, a single well or combination of wells can be used. This allows convenient application or retrieval of individual samples, or of samples from selected lanes.

In another embodiment, a line applicator/retriever is provided. This has a single well which extends the width of the gel. It allows the application of a single sample on a slab gel in the form of a homogeneous line. Application of a single line across the gel is desirable for preparative and semi-preparative gels, where sample volumes are large. A line sample can also be used in transverse pH-gradient gels or transverse gradient pore gels. For two-dimensional gels, the sample may be retrieved from the first dimension, then loaded directly on the second gel, eliminating the need for inconvenient second loading procedures.

A sample concentrator may be employed as an applicator if the sample volume is large or additional separation steps are desired. The concentrator provides an extension of the upper portion of the well, conveniently in the shape of a cone, having a stacking gel at the lower portion of the well. The volume of sample will usually be in the range of about 0.5 to 10 ml, while the entire well will have a volume of up to 25 ml. By having an array with a plurality of wells, each with a common stacking gel, each of the lanes can receive a sample simultaneously. Alternatively, one may have different stacking gels and/or different buffers where the concentration times will be different.

An electrode is provided proximal to the top of the well for providing a voltage gradient between such electrode and an electrode in the gel for stacking of the sample and transferring the concentrated sample to the gel. By the appropriate choice of the buffer ions, one may select the nature of the components in the gel which will be concentrated and transferred to the gel. Thus, a highly concentrated sample is transferred to the gel to provide for better resolution.

Turning now to the drawings, FIG. 1A is a perspective view of the multiwell applicator/retriever, preferably formed of a transparent material to simplify the loading and monitoring of samples. The device consists of an electrode bar 7 and a multiwell device 5. For applying samples, only the multiwell device is used. The multiwell device 5 is a block consisting of a linear array of wells 8. Each well 8 is open at the top and bottom. The top of the well 17 forms an entry port. The bottom of the well forms the sample nozzle 6. Samples are applied through the entry port 17 with a suitable device. The pegs 13 allow the applicator to rest on, or fit into a gel apparatus or loading mechanism support.

Figure 1B:
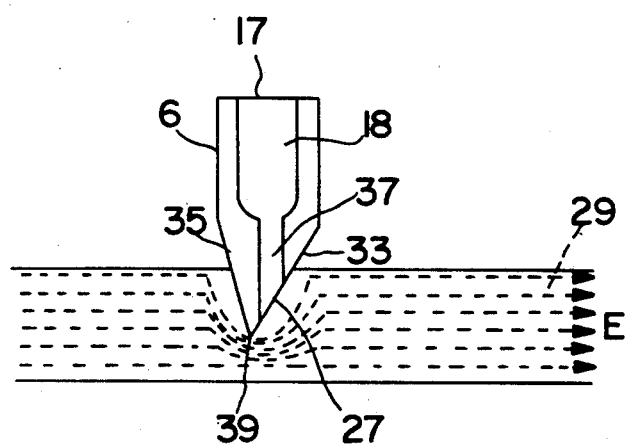
FIG. 1B, shows a cross-sectional view along line 1B of the sample nozzle, including a diagrammatic representation of a gel and electric field lines.

FIG. 1B is a cross-sectional view along lines 1B—1B showing the nozzle 6 and a diagrammatic representation of a gel. The nozzle forms the lower end of the well 17. The nozzle is triangular when viewed in cross-section orthagonal to the array of wells. It comes to a point 39, which is inserted into the gel matrix 29. The front face of the triangle 33 and the aperture 27 are optimized to cause a sample to evenly disperse when loaded onto a gel 29. The back face of the nozzle 35 is designed to minimize the volume of space occupied by the nozzle.

The sample applicator may be used as a retriever with the addition of the retrieval electrode. The electrode may be embedded in the applicator, or it may be on a removable electrode retrieval bar 7. The retrieval bar is an electrically non-conductive bar 21, roughly the length of the applicator device. It has attached to it an electrode assembly consisting of an electrode connecter 24 attached to a wire 23 leading to partially embedded contact electrodes 25. The contact electrodes may be formed of any electrically conducting material, preferably graphite or a metal wire, such as platinum. They are shaped to form an array of rectangles 25, in which the number of rectangles is usually equal to the number of wells in the applicator. The retrieval bar is placed on top of the applicator wells, such that each contact electrode fits into a well. The rectangles 25 extend out of the bar, such that the contact electrode extends into the top of the well 17.

The well 17 may be filled with electroconductive media 18, and the bottom of the well sealed with retrieval matrix 37. The gel 29, matrix and/or media, and electrode are in electrical communication. If media or matrix is present, then when the nozzle is inserted into the gel, a current flow may be established between the contact electrode 25 and one other electrode in the gel apparatus. This draws the sample to be retrieved into the matrix, from where it may easily be recovered without the necessity for disrupting the gel material.

Figure 2A:
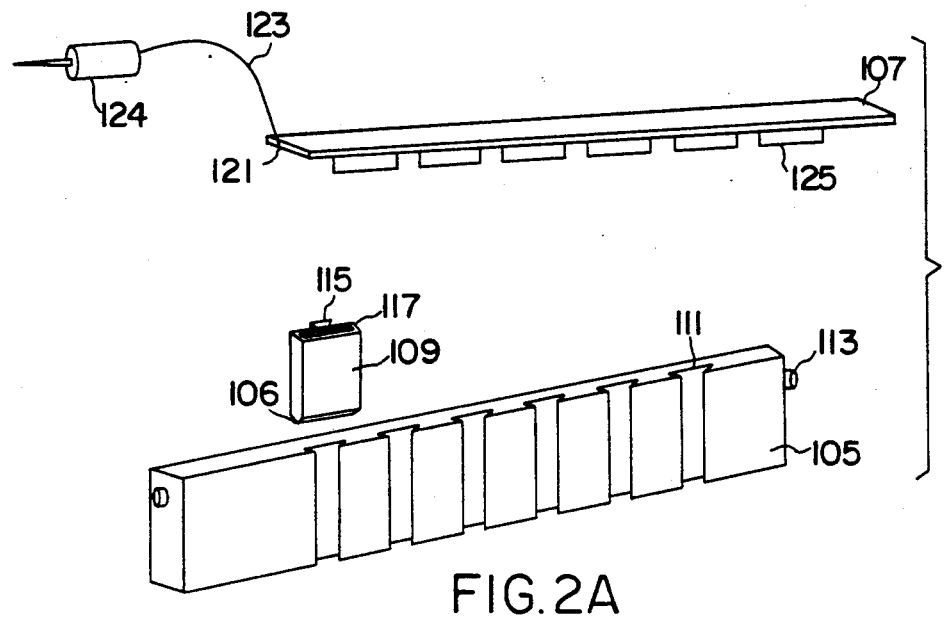
FIG. 2A is a perspective view of the individual well applicator/retriever.
Figure 2B:
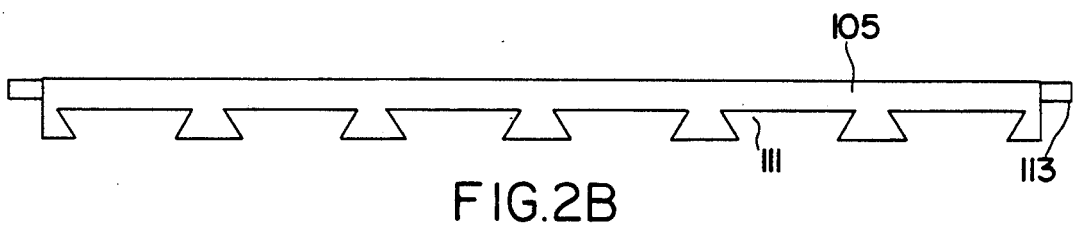
FIG. 2B shows a top view of the mounting bar.
Figure 2C:
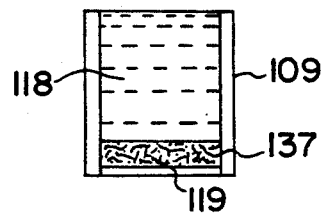
FIG. 2C shows a cross-sectional view of an individual well casing.

FIG. 2A is a perspective view of an individual well applicator/retriever. The device has a mounting bar 105, an electrode bar 107 and a plurality of individual well casings 109. The mounting bar is a bar 105 with grooves 111 along one side, and pegs 113 on the ends. A cross-sectional view of the mounting bar is shown in FIG. 2B. The pegs 113 allow the mounting bar to rest on, or fit into a gel apparatus or loading mechanism support. Each groove 111 in the mounting bar fits firmly with a notch 115 on an individual well casing 109, and will hold it in place. A cross-sectional view of an individual well is shown in FIG. 2C. Each individual well casing 109 has a well 117 which is open at the top and the bottom. The bottom of the forms a sample nozzle 106. The sample nozzle 106 is inserted into the gel, as described in FIG. 1B. Samples are applied through the top of the well 117 with a suitable device.

The sample applicator may be used as a retriever with the addition of a retrieval electrode, as described for the multiwell applicator. The electrode may be embedded in the applicator, or it may be on a removable electrode retrieval bar 107. The retrieval bar is an electrically non-conductive bar 121, roughly the length of the applicator device. It has attached to it an electrode assembly consisting of an electrode connecter 124 attached to a wire 123 leading to partially embedded contact electrodes 125. The retrieval bar is placed on top of the applicator wells, such that each contact electrode 125 either fits into a well or an empty groove. For retrieval of selected samples from a gel, well casings may be in place only for those tracks from which samples are to be retrieved.

The well 117 may be filled with electroconductive media 118, and bottom of the well sealed with retrieval matrix 137. The gel, matrix and/or media, and electrode are in electrical communication. If media or matrix is present, then when the nozzle is inserted into the gel, a current flow may be established between the contact electrode 125 and one other electrode in the gel apparatus.

Figure 3A:
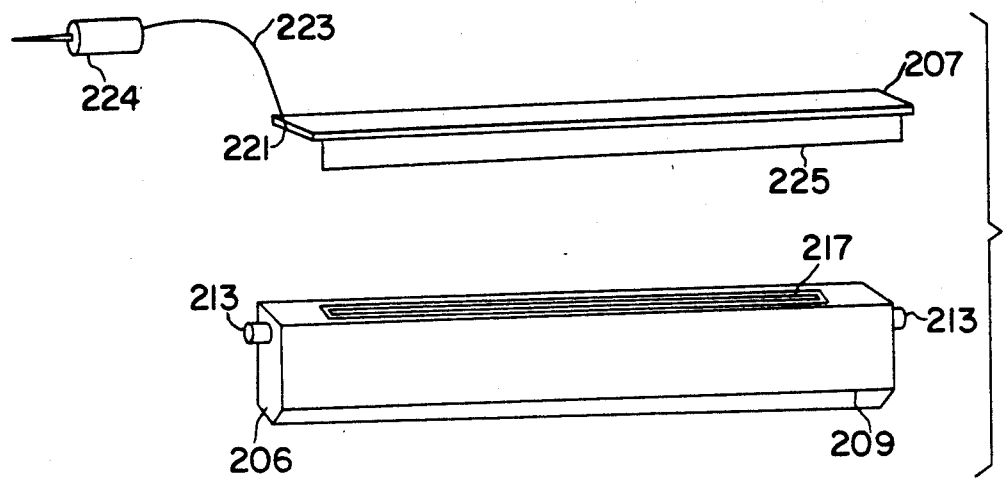
FIG. 3A is a perspective view of the line applicator/retriever.
Figure 3B:
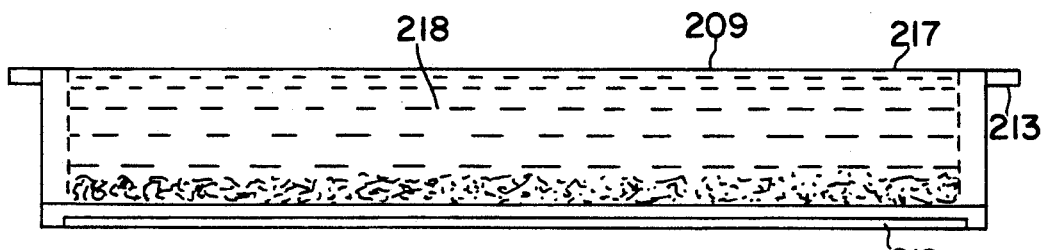
FIG. 3B shows a cross-section of the line well.

A line applicator/retriever is also provided. FIG. 3 is a perspective view of the line applicator/retriever. The device consists of an electrode bar 207 and a line well casing 209. The line well casing is a block 209 with pegs 213 on the ends. A cross-sectional view of the well casing is shown in FIG. 3A. The well casing 209 has a single well 217 which is open at the top and bottom. The bottom of the well forms a sample nozzle 206, as described in FIG. 1B. Samples are applied through the top of the well 217 by a suitable mechanism.

The applicator may be used as a retriever with the addition of a retrieval electrode, as described for the multiwell applicator. The electrode may be embedded in the applicator, or it may be on a removable electrode retrieval bar 207. The retrieval bar is an electrically non-conductive bar 221, roughly the length of the applicator device. It has attached to it an electrode assembly consisting of an electrode connecter 224 attached to a wire 223 leading to partially embedded contact electrode 225. The retrieval bar is placed on top of the applicator well, such that the contact electrode 125 fits into the well.

The well 117 may be filled with electroconductive media 118, and the bottom of the well sealed with retrieval matrix 137. The gel, matrix and/or media, and electrode are in electrical communication. If media or matrix is present, then when the nozzle is inserted into the gel, a current flow may be established between the contact electrode 125 and one other electrode in the gel apparatus.

Figure 4:
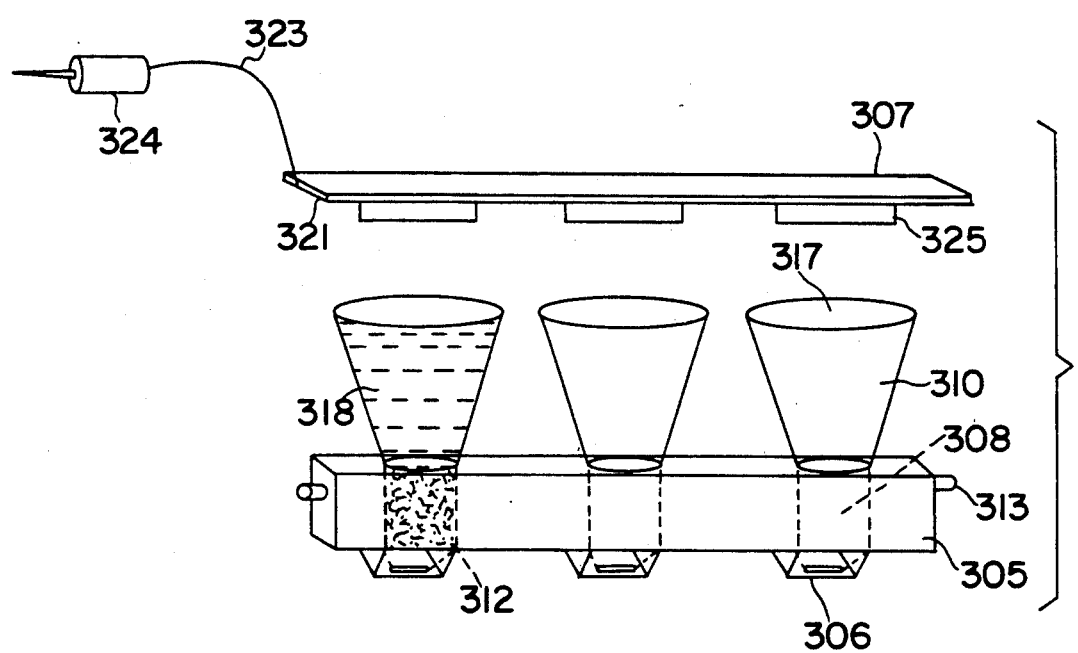
FIG. 4 is a perspective view of the concentrator applicator.

FIG. 4 is a perspective view of the sample concentrator applicator. The device consists of an electrode bar 307 and a concentrator applicator 309. The concentrator applicator is a block 309 consisting of a linear array of wells 308. Each well 308 is open at the top and bottom. The top of the well 317 forms a concentrator funnel. The bottom of the well forms a sample nozzle, as described in FIG. 1A. Samples are applied through the top of the funnel 317. The well 308 may be filled with electroconductive media 318 and concentration or separation matrix at the bottom 312.

The electrode may be embedded in the applicator, or on a separate bar 307. The electrode bar is a bar 321 with an electrode connecter 324 attached to a wire 323 attached to partially embedded contact electrodes 325. The retrieval bar is placed on top of the concentrator wells, such that the contact electrodes 125 fits into the wells, and can come into contact with the electroconductive media 318 in the well. The contact electrode 325 provides a voltage gradient between itself and an electrode in the gel, for stacking the sample and transferring the concentrated sample to the gel.

The applicator/retriever allows for improved methods of carrying out gel electrophoresis. By being able to apply a sample at any desired position on the gel and retrieve a band at any position on the gel, particularly during the course of the gel electrophoresis, increased flexibility in carrying out gel separations is achieved.

In accordance with the method, the sample may be introduced directly into the gel by use of the applicator/retriever, where different and/or the same samples may be simultaneously introduced into different lanes of the gel, or a single sample may be introduced across the gel. The applicator/retriever may then be removed, with gel healing so as to fill the gap created by the nozzle, and the electrophoresis initiated. During the course of the electrophoresis, the applicator/retriever may be once again introduced into the gel, and with the electrode accompanying the applicator/retriever a band electroeluted into the applicator/retriever. The electrophoresis may then proceed, while the extracted component is processed or used, as appropriate. In this manner, one does not need to wait for the electrophoresis to be completed before removing one or more bands, but can remove a band during the course of the electrophoresis without disturbing the reproducibility of the migration of the other components in the sample.

With the applicator/retriever, one can insert the applicator/retriever into a gel at a site where a band is visible or cannot be discerned, but is expected to be at a certain position. For example, by using molecular weight standards, one may expect a particular component to have migrated a similar distance as the standard. By placing the retriever adjacent that position in the sample lane, one can electroelute the component, if present. One can place the applicator/retriever at different sites to determine whether there is any component in the sample which migrates similarly to a standard composition or has a molecular weight or migration rate. Where a large band or smeared band is observed or obtained, the band may be removed and used for a second gel electrophoresis to provide better separation. Thus, rather than waiting for the completion of the electrophoresis to cut out the gel portion having the band, isolating the sample components and introducing the sample components into another gel for electrophoresis, one can remove the band during the electrophoresis and directly transfer the components in the band to a second gel with the applicator/retriever.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A gel electrophoresis sample applicator/retriever device comprising:
   a holder comprising a linear array of wells or mountings for detachably mounting individual wells, with the proviso that when said holder comprises said mountings, said device further comprises a plurality of wells capable of being detachably mounted to said holder;
   said wells comprising a channel and forming a nozzle at a bottom end having a front and rear face, said front and rear faces being angled to form an edge transverse to a gel surface in the direction of component migration in said gel, and said front face having an aperture in communication with said channel, which aperture serves to release sample components substantially uniformly into a gel under the influence of an electrical field when said nozzle is inserted into a gel; and
   a retrieval electrode for inserting into said channel.

2. A device according to claim 1, wherein said retrieval electrode is capable of removable insertion into said channel.

3. A device according to claim 1, wherein said wells are detachably mounted on said holder.

4. A device according to claim 1, wherein said aperture extends substantially across said front face.

5. A device according to claim 1, further comprising a concentrator funnel capable of mounting on said channel and partially extending into said channel.

6. A device according to claim 1, wherein said front face is at an angle of from about 53 to 58 degrees and said back face at an angle of from about 62 to 67 degrees to a gel surface when said device is held upright.

7. A gel electrophoresis sample applicator/retriever device comprising:
   a holder comprising a linear array of wells;
   said wells comprising a channel and forming a nozzle at a bottom end having a front and rear face, said front and rear faces being angled to form an edge transverse to a gel surface in the direction of component migration in said gel, and said front face having an aperture in communication with said channel, which aperture serves to release sample components substantially uniformly into a gel under the influence of an electrical field when said nozzle is inserted into a gel, wherein said front face is at an angle of from about 53 to 58 degrees and said back face at an angle of from about 62 to 67 degrees to a gel surface when said device is held upright; and
   a retrieval electrode for inserting into said channel.

8. A device according to claim 7, comprising pegs at each end of said holder for mounting said holder on a support.

9. A device according to claim 7, wherein said holder is of clear plastic.

10. A device according to claim 7, wherein said holder further comprises an electrode extending into a well.

11. A method for performing a gel electrophoresis with removal of at least one band during the course of the electrophoresis prior to completion of said electrophoresis, employing a gel electrophoresis sample applicator/retriever device comprising:
    a holder comprising a linear array of wells or mountings for detachably mounting individual wells, with the proviso that when said holder comprises said mountings, said device further comprises a plurality of wells capable of being detachably mounted to said holder;
    said wells comprising a channel and forming a nozzle at a bottom end having a front and rear face, said front and rear faces being angled to form an edge transverse to a gel surface in the direction of component migration in said gel, and said front face having an aperture in communication with said channel, which aperture serves to release sample components substantially uniformly into a gel under the influence of an electrical field when said nozzle is inserted into a gel; and a retrieval electrode for inserting into said channel; said method comprising:

inserting said nozzle into said gel while maintaining an electrical field in said gel, whereby components in said sample migrate into said gel;

maintaining an electrical field in said gel, whereby said components migrate and separate in said gel to define bands;

inserting said nozzle containing an electrically conducting medium into said gel adjacent at least one parallel band and applying an electrical field between said electrode inserted in said channel and a second electrode opposite said band from said nozzle, whereby said component in said band migrates into said medium; and removing said nozzle from said gel.

* * * * *